United States Patent [19]

Huffman et al.

[11] Patent Number: 4,935,021

[45] Date of Patent: Jun. 19, 1990

[54] DISPOSAL DIAPER WITH CENTER GATHERS

[75] Inventors: Gloria Huffman, Federal Way; Heinz A. Pieniak, Des Moines, both of Wash.

[73] Assignee: McNeil-PPC, Inc., Milltown, N.J.

[21] Appl. No.: 263,260

[22] Filed: Oct. 27, 1988

[51] Int. Cl.⁵ .............................................. A61F 13/16
[52] U.S. Cl. ................................ 604/385.1; 604/385.2
[58] Field of Search ................. 604/385.1, 385.2, 378, 604/358

[56] References Cited

U.S. PATENT DOCUMENTS

| | | | |
|---|---|---|---|
| 2,538,758 | 1/1951 | Bricmont | 604/347 |
| 3,954,107 | 5/1976 | Chesky et al. | 604/385.1 |
| 4,050,462 | 9/1977 | Woon et al. | |
| 4,323,070 | 4/1982 | Ternström et al. | 604/385.2 |
| 4,430,086 | 2/1984 | Repke | |
| 4,573,988 | 3/1986 | Pieniak et al. | |
| 4,582,550 | 4/1986 | Sigl | 604/385.2 X |
| 4,605,404 | 8/1986 | Sneider | 604/385.1 |
| 4,655,760 | 4/1987 | Morman et al. | 604/385.2 |
| 4,661,102 | 4/1987 | Shikata et al. | |
| 4,662,877 | 5/1987 | Williams | 604/385.2 |
| 4,743,245 | 5/1988 | Lassen et al. | 604/385.1 |
| 4,753,645 | 6/1988 | Johnson | 604/385.1 X |
| 4,775,375 | 10/1988 | Aledo | 604/378 |
| 4,804,380 | 2/1989 | Lassen et al. | 604/385.1 |
| 4,838,885 | 6/1989 | Bernardin | 604/368 X |
| 4,892.536 | 1/1990 | Des Marais et al. | 604/385.2 |
| 4,895,568 | 1/1990 | Enloe | 604/385.2 |

Primary Examiner—Richard J. Apley
Assistant Examiner—Rachel M. Healey
Attorney, Agent, or Firm—Dressler, Goldsmith, Shore, Sutker & Milnamow, Ltd.

[57] ABSTRACT

An absorbent article embodied as a disposable diaper construction has been particularly configured for improved fit and comfort by the provision of a center gathering arrangement. In the illustrated embodiments, the diaper includes an absorbent panel structure which is positioned between associated facing and backing layers, and further includes an arrangement of one or more elastic elements which extend longitudinally of the diaper. By this arrangement, a longitudinal gathering force is created on the absorbent panel of the diaper, whereby the diaper is shortened to improve its fit, thus enhancing comfort for the wearer as well as inhibiting leakage from the diaper.

18 Claims, 5 Drawing Sheets

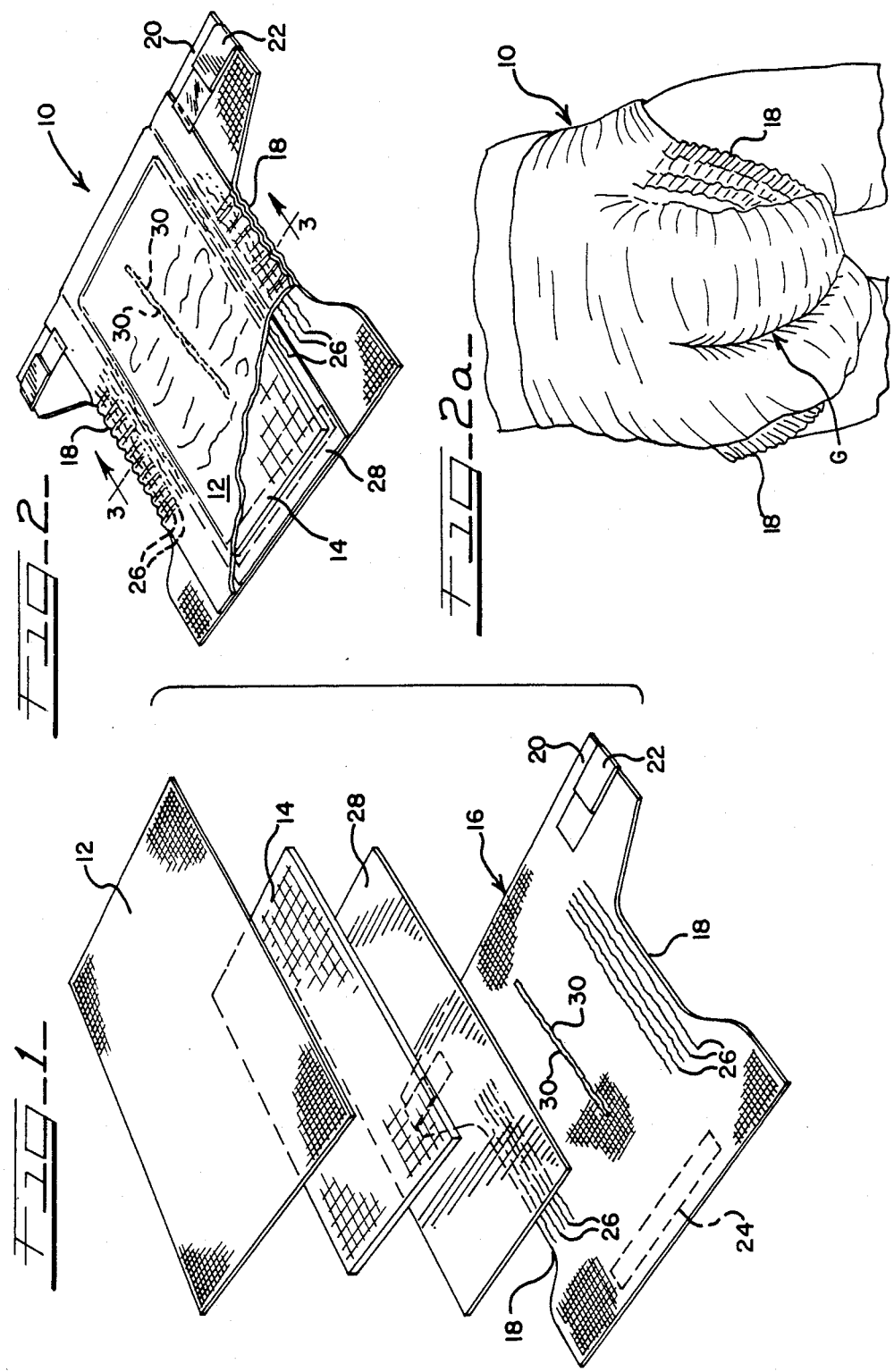

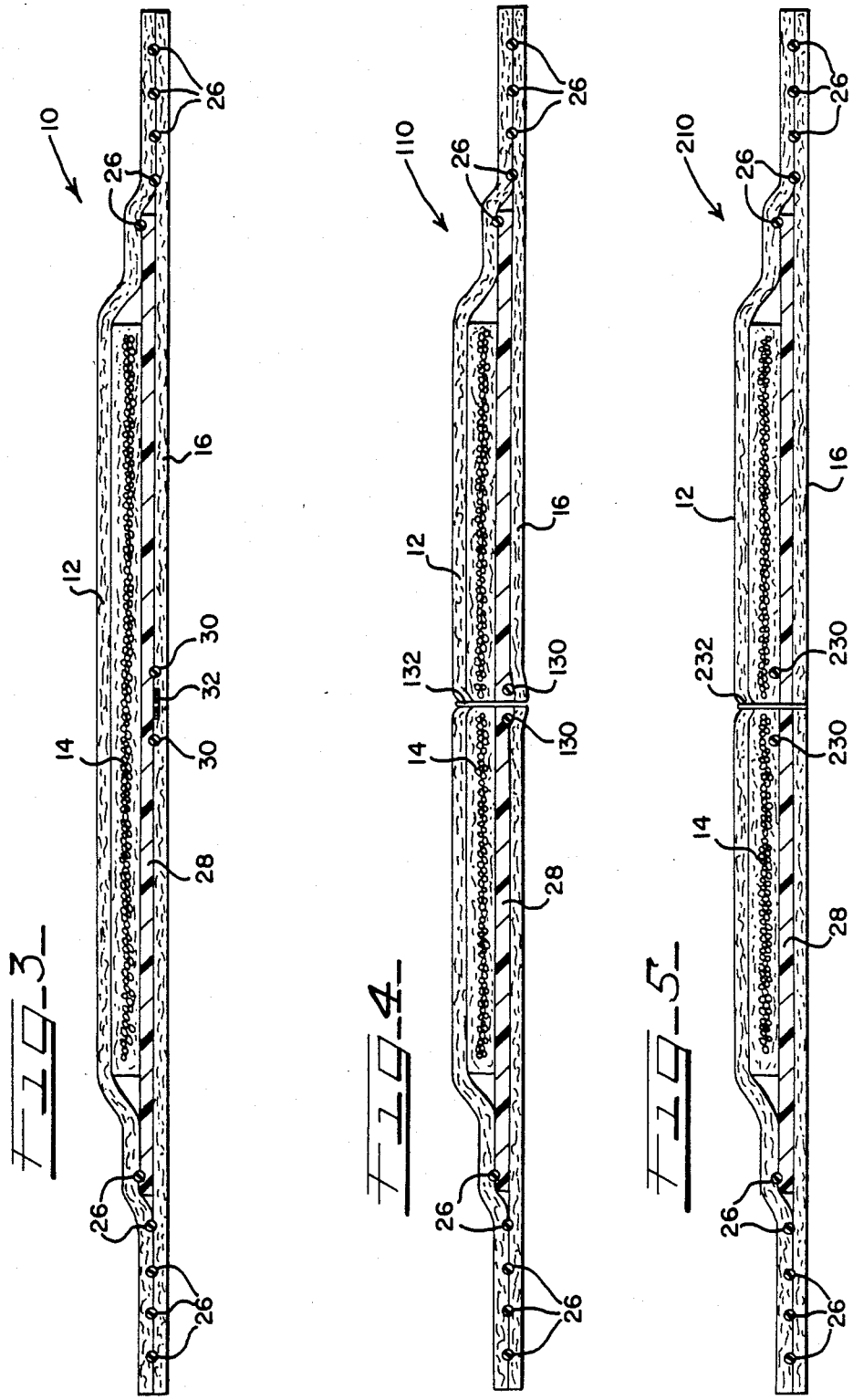

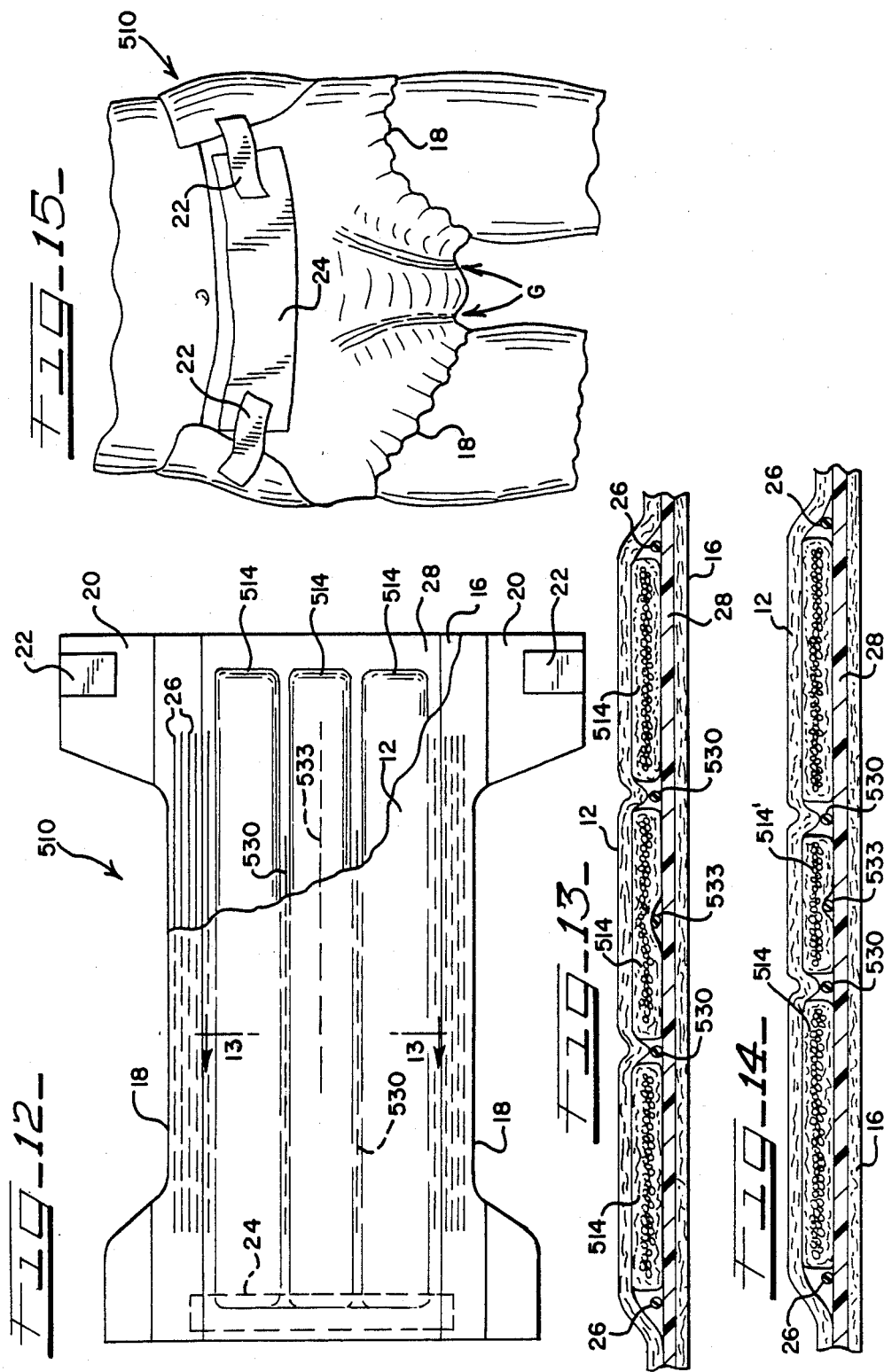

DISPOSAL DIAPER WITH CENTER GATHERS

TECHNICAL FIELD

The present invention relates generally to disposable absorbent articles, and more particularly to an absorbent article such as a disposable diaper including an arrangement for providing a longitudinal gathering force on the absorbent panel of the article, whereby the article is longitudinally gathered, inwardly of its side margins, for improved fit and comfort for the wearer.

BACKGROUND OF THE INVENTION

Disposable diapers are now in very widespread use for baby and infant care. Diapers of this nature are ordinarily configured for a single use, with an absorbent panel or core of the diaper typically provided in an integrated structure including a moisture-pervious facing layer and a typically moisture-impervious backing layer. Adhesive-coated tape tabs and the like facilitate convenient fitting of a diaper to a baby, with the advent of elasticized portions at the leg openings of the diaper (sometimes referred to as "leg gathers") further conforming the diaper article to the baby for improved fit and comfort. While disposable diapers sized for infant and baby care are extremely popular, adult-sized disposable diapers have also been improved to exhibit improved absorbency and fit for convenient and comfortable use by incontinent adults.

The provision of leg gathers in a disposable diaper desirably enhances the fit and comfort of the diaper, while at the same time desirably acting to abate any leakage of the diaper by conforming the leg openings to the wearer. Such leg gathers are typically provided by incorporating one or more elastic elements generally at the side margins of the diaper, with these elastic elements creating a gathering force at the side margins, and particularly at the side marginal portions of the facing and backing layers, to achieve the desired fit. As a consequence of these localized gathering forces, the portion of the diaper generally inwardly of the edges of the absorbent panel is not subjected to gathering to the same degree as the side margins of the diaper. As a result, this portion of the diaper, and particularly that portion between the legs of the wearer and rearwardly thereof at the seat of the diaper, exhibits a very pronounced tendency to sag or droop, with the diaper assuming a generally baggy appearance. Again, this is most pronounced in diapers having elasticized leg bands at the side margins, with the side margins shortening under the influence of the elastic means while the center or medial portion of the diaper essentially remains at its original length.

As will be appreciated, this pronounced bagginess of the typical disposable diaper construction, and the resultant bulkiness between the wearer's legs, interferes with the wearer's movements, and undesirably exposes the typically plastic moisture-impervious backing layer to the inside of the wearer's thighs. Additionally, outer clothing fits very poorly over such a diaper, further reducing the comfort of the infant or other wearer.

Accordingly, it is very desirable to provide an arrangement which enhances the comfort and fit of a disposable diaper by reducing the typical bagginess which such diapers exhibit. In accordance with the present invention, an absorbent article such as a disposable diaper is disclosed which is configured to effect a longitudinal shortening or gathering of the central portion of the diaper, thus providing enhanced fit and comfort.

SUMMARY OF THE INVENTION

A disposable diaper or other absorbent article embodying the principles of the present invention has been particularly configured for improved fit and comfort by providing a center gather arrangement which exerts a longitudinal gathering force on the absorbent panel of the diaper, apart from any gathering effected by elastic leg gathers or the like which the diaper may include. The center gathers preferably effect the longitudinal gathering along the middle one-third to one-half of the absorbent panel/, width-wise, while leaving the lateral side margins of the panel substantially ungathered by the center gathers. This center gathering force is created by providing one or more elastic members or elements in operative association with the central portion of the absorbent panel of the diaper. In accordance with certain aspects of the invention, the absorbent panel may comprise a plurality of laterally adjacent, discrete panel sections, thus facilitating the desired longitudinal gathering, improved fit, comfort, and liquid retention are achieved while the absorptive characteristics of the diaper are maintained.

In the illustrated embodiments, the present disposable diaper is shown as including a generally elongated absorbent panel which may comprise any of a large number of different absorbent materials and structures, including fiber elements, fibrous matrices, and so-called superabsorbent hydrocolloid materials. The present diaper further includes a facing layer which is positioned on one side and overlies the absorbent panel, with the facing layer adapted for positioning adjacent to the wearer of the diaper.

The present diaper construction further includes a backing layer positioned on the other side of the absorbent panel opposite the facing layer. While many different arrangements may be employed while keeping with the principals disclosed herein, the illustrated embodiment includes a fluid-pervious material, such as nonwoven fabric, which may be similar to that from which the facing layer is formed, thus enhancing the "breathability" of the diaper structure. If desired, the nonwoven fabric of the backing layer is not treated with a surfactant, to thus maintain the typical hydrophobicity of the material. The desired liquid retention can be achieved by the provision of a substantially fluid-impervious barrier layer which underlies the absorbent panel, and is positioned between the absorbent panel and the backing layer. This barrier layer may comprise a separate sheet of fluid-impervious material, or suitable fluid-impervious material applied to the backing layer.

In the preferred form, each side margin of the diaper is provided with leg-gathering elastic elements, or equivalent means, which are positioned generally at the laterally opposite margins of the diaper to conform the diaper to the legs of the wearer. In the illustrated embodiments, a plurality of individual elastic elements are provided at the laterally opposite margins of the diaper to provide the preferred leg gathers at these regions.

As discussed above, the preferred provision of leg gathers in a disposable diaper structure can sometimes result in a bagginess or bulkiness for the structure at the middle width portion thereof, generally between and inwardly of the side margins of the absorbent panel of the diaper. In accordance with the present invention, a center gathering arrangement is provided in operative association with the diaper absorbent panel for providing a longitudinal gathering force to conform the diaper to the wearer for improved fit and comfort. In the preferred form, the center gathering arrangement comprises one or more elastic members, or equivalent elements, which can be positioned generally along the longitudinal centerline of the diaper, and/or on respective opposite sides thereof, so that the gathering force created thereby acts to shorten or gather the diaper along in the region of its longitudinal centerline. By virtue of this arrangement, the absorbent panel of the diaper, as well as its associated facing layer and preferably the backing layer, are contracted in a manner which improves the diaper's fit, and alleviates bagginess or sagging at the central portion of the diaper.

In one illustrated embodiment, the center gathering arrangement comprises at least one elastic member positioned in operative association with the absorbent panel of the diaper, and extending generally along the longitudinal centerline thereof. The absorbent panel generally comprises a front panel portion, a rear panel portion, and a central panel portion extending therebetween, each of which portions generally correspond to front, central, and rear thirds of the absorbent panel structure. Preferably, the elastic member is positioned rearwardly of the front panel portion, and extends along the central and rear panel portions, i.e., generally along the seat portion of the diaper.

For the purposes of the present discussion, reference to elastic members or the like is intended to encompass elastic materials, pre-stretched monofilament strands, polyurethane films or foams, elastomeric foams, shrink film, and other materials and structures which can be arranged to exert a gathering force on the associated diaper components. Various arrangements may be employed for securing the elastic components of the center gathers in position, including suitable adhesive, ultrasonic bonding, heat-sealing, and the like.

In further embodiments of the present absorbent article, the absorbent panel comprises a plurality of laterally adjacent, discrete panel sections. Such arrangements facilitate the desired improved fit and comfort of the article, by the conformance of the panel sections to the wearer under the influence of the longitudinal gathering provided by the center gathering means.

In one embodiment, a pair of adjacent panel sections are provided, with the center gathers provided in the form of at least one longitudinally extending elastic member positioned at the adjacent inner edges of the panel sections, generally at the longitudinal centerline of the article. Such an arrangement not only provides the desired fit and comfort characteristics when the absorbent article comprises a diaper, but further can be configured as a sanitary napkin or the like with enhanced fit and comfort.

In other embodiments, the absorbent panel of the article comprises a center panel section, and a pair of laterally adjacent side panel sections positioned on respective opposite sides of said center panel section In these constructions, the center gather arrangement preferably comprises an elastic member positioned generally at the adjacent edges of each adjacent pair of panel sections, i.e., generally at the respective opposite edges of the center panel section. To further enhance the fit characteristics, the center gather arrangement can further comprise another elastic member positioned beneath the center panel section, generally along the longitudinal centerline of the article.

Other features and advantages of the present invention will become readily apparent from the following detailed description, the accompanying drawings, and the appended claims.

BRIEF DESCRIPTION OF THE DRAWINGS

FIG. 1 is an exploded perspective view of an absorbent article, shown as a disposable diaper, embodying the principles of the present invention;

FIG. 2 is a perspective view of the disposable diaper of FIG. 1;

FIG. 2a is an illustration of a disposable diaper embodying the present invention fitted to a wearer;

FIG. 3 is a cross-sectional view taken generally along lines 3-3 of FIG. 2;

FIG. 4 is a cross-sectional view similar to FIG. 3 illustrating an alternate construction for the present disposable diaper;

FIG. 5 is a cross-sectional view similar to FIG. 3 illustrating a further alternate construction for the present disposable diaper;

FIG. 12 is a top plan view of a further alternate embodiment of a disposable diaper embodying the present invention;

FIG. 13 is a cross-sectional view taken generally along lines 13-13 of FIG. 12;

FIG. 14 is a view similar to FIG. 13 illustrating a further modified embodiment of the present invention; and FIG. 15 is an illustration showing another disposable diaper embodying the present invention fitted to a wearer.

DETAILED DESCRIPTION

Figure 6:
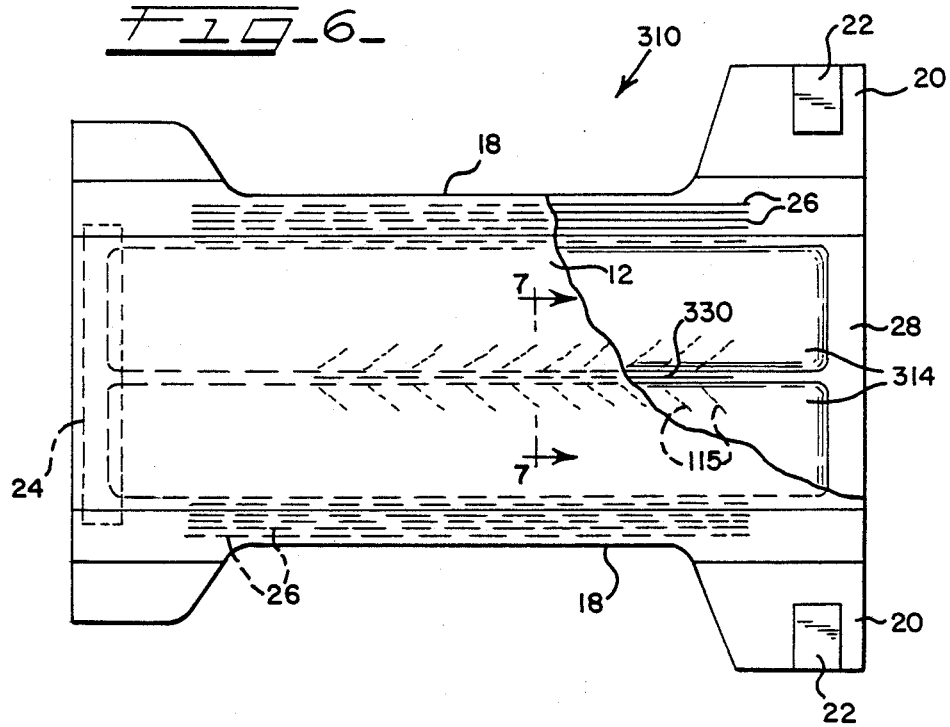
FIG. 6 is a top plan view of a further alternate construction for the present disposable diaper.

While the present invention is susceptible of embodiment in various forms, there is shown in the drawings and will hereinafter be described alternate embodiments of the invention, with the understanding that the present disclosure is to be considered as an exemplification of the invention, and is not intended to limit the invention to the specific embodiments illustrated.

Referring first to FIGS. 1 and 2, therein is illustrated an absorbent article shown as a disposable diaper 10 embodying the principles of the present invention. As used in the present disclosure, the term diaper is intended to refer to an absorbent article which is worn by an individual for absorbing urine and/or fecal matter. It is to be understood that diapers embodying the principles of the present invention can be appropriately sized for use by infants or babies, and can further be sized for use by incontinent adults. Furthermore, absorbent articles embodying the present invention may take the form of sanitary products, or absorbent diaper inserts.

In the preferred form, the disposable diaper 10 of the present invention includes a facing layer 12 formed from a moisture-pervious material which is adapted to be positioned adjacent to the infant or other wearer of the diaper. As will be recognized by those familiar with the art, several different types of materials may be used for the fluid-pervious facing layer 12. For example, the facing layer may comprise a non-woven web made of a mixture of fibers consisting predominantly of inexpensive, short, cellulosic fibers such as short wood pulp fibers or cotton linters in amounts of 75% to 98%, the balance being textile length fibers such as rayon, as described in U.S. Pat. No. 3,663,348, to Liloia, et al.

Non-woven facing layer materials suitable for use in disposable diapers in accordance with the present invention can have fabric weights in the range of from about 0.3 to 5 ounces per square yard and densities of less than 0.15 grams per cc, generally in the range of 0.05 to about 0.1 grams per cc. The dry strength of the facing layer for a fabric having a weight of about 1.5 ounces per square yard is at least 0.15 pounds per square inch of width in the machine direction, and at least 0.1 pounds per square inch of width in the cross direction. Such fabrics have good elongation, loft, softness, and drape characteristics.

Facings may also be made of an apertured non-woven fabric which is formed, for example, in accordance with the teachings of U.S. Pat. Nos. 2,862,251, 3,081,513, and 3,081,515. Furthermore, facings may also be made from other types of fabrics such as those disclosed and described in U.S. Pat. No. 3,485,706, to Evans. Such facings can be made of naturally occurring fibers, synthetic fibers, or blends thereof. For example, the fabric may be polyester, polyethylene, polypropylene, nylon, rayon, or the like. Typical facing sheets made of polypropylene type fabrics may have a weight of about 0.7 ounces per square yard.

In addition, facings may be made from non-apertured materials such as non-woven isotropic webs or apertured polyolefin or polyester films having the desired moisture permeability. Spun-bonded and melt-blown fabrics can also be employed. In all the aforementioned facings, the materials should be relatively hydrophobic so as to retard wicking within the facing layer.

As will be appreciated, a variety of different materials may be employed for the fluid-pervious facing layer 12. While the facing layer is fluid-pervious (i.e., moisture-permeable), it is preferably of the type which after permeation by moisture, prevents strike-back of body fluid when the absorbent structure associated with the facing layer is approaching saturation.

In the illustrated embodiment, the associated absorbent structure is provided by a generally rectangular absorbent panel 14, with the facing layer 12 positioned adjacent to and overlying one side or surface of the absorbent panel. The absorbent panel 14 may comprise any of a variety of well known absorbent structures, including ones having loosely compacted, short cellulosic fibers, such as wood pulp fibers, or cotton linters, or mixtures thereof, which are primarily held together by interfiber bonds requiring no added adhesive, as is known in the art. Further, absorbent structures incorporating so-called superabsorbent hydrocolloid materials may be employed. Composite absorbent structures, employing fibrous material as well as superabsorbent compounds, may likewise be used, such as disclosed in U.S. Pat. No. 4,573,988, to Pieniak, et al.

For the present disclosure, reference will be made to a front, central, and rear portions of the absorbent panel 14. It is to be understood that these panel portions generally correspond to the front one-third, the central one-third, and the rear one-third of the absorbent panel 14.

Referring again to the drawings, diaper 10 includes a backing layer 16 positioned on the other side or surface of the absorbent panel 14, i.e., generally opposite the facing layer 12. Thus, the absorbent panel 14 is positioned in sandwich-like relation between the facing and backing layers. In the illustrated embodiment, backing layer 16 is provided in a generally I-shaped form, and thus defines leg cutouts 18 at the laterally opposite side margins thereof, and further defines a pair of laterally projecting ears 20 generally at the rearward portion of the layer. In the preferred construction, adhesive tape closures 22 are preferably secured to each of the ears 20 of the backing layer 16, with the tape closures configured for releasable securement to a tape-receiving strip 24 affixed to the outer, forward surface of the backing layer.

In order to conform the diaper 10 to the legs of the wearer for comfort, as well as good liquid retention, a plurality of elongated leg gathering elastic elements 26 are provided generally at each of the laterally opposite side margins of the diaper in the region of leg cutouts 18. The plurality of elastic elements 26 cooperate to conform the diaper to the wearer without undue pressure being applied to the wearer's skin. In the illustrated embodiment, the elastic elements 26 are positioned between facing layer 12 and backing layer 16.

As is known in the art, absorbent panel 14 can be secured in position such as by spaced, parallel glue lines, with facing layer 12 secured to backing layer 16 outwardly of the absorbent panel such as by glue lines, sonic welding, or other bonding means as may be appropriate, depending upon the particular materials employed for the diaper construction. While the backing layer 16 may comprise a substantially moisture-impervious material such as polyethylene, it is presently preferred that the backing layer 16 be formed of a fluid-pervious material generally of the type from which the facing layer 12 is formed, as described hereinabove, except backing layer 16 is preferably more hydrophobic than the facing layer to repel urine. By such an arrangement, the diaper is provided with improved breathability for the comfort of the wearer.

In order to prevent leakage of liquid from the absorbent panel 14 through the backing layer 16, a substantially moisture-impervious barrier layer 28 is provided between the panel 14 and the backing layer 16, with the barrier layer 28 underlying the absorbent panel 14 and having a surface less than that of backing layer 16. The barrier layer 28 may be formed a separate sheet of from suitable moisture-impervious material such as polyethylene having a thickness on the order of 0.0005–0.001 inches. Other suitable flexible moisture-impervious materials may be used in accordance with the invention, such as for example, polyethylene terephthlate sheet having a thickness of approximately 0.0005–0.001 inches. Additionally, coatings of liquid-impervious material, such as hot-melt adhesives, or hydrophobic coatings of silicone or fluorocarbon compounds, can be applied to the backing layer 16 to provide the desired barrier properties. By this arrangement, the occluded area of the diaper is minimized. It is also possible to employ liquid-impervious, vapor-pervious fabrics and films, as are known in the art, for the backing layer.

In the illustrated embodiment, the innermost pair of elastic elements 26 are positioned inwardly of the respective lateral edges of barrier layer 28, between the barrier layer and the facing layer 12.

In accordance with the present invention, a center gather arrangement is provided whereby a longitudinal gathering force is provided on the absorbent panel 14 of the diaper 10, with the gathering force effecting a shortening of the diaper generally along its longitudinal centerline. While the specific type of elastic material employed for the center gathers can be widely varied while keeping with the teachings herein, it will be appreciated that a principal object of providing the center gathers is to effect shaping of the diaper or other article. As will be further appreciated, the one or more elastic elements employed in achieving the desired gathering and shaping can be arranged linearly or non-linearly, either in parallel or non-parallel relationship to the longitudinal centerline of the absorbent article.

In this embodiment, the desired gathering force is created by elastic means positioned generally rearwardly of the front portion of the absorbent panel 14, with the elastic means extending longitudinally of the diaper generally at its centerline. In this illustrated embodiment, the gathering force is provided by a pair of generally parallel elastic members 30, which members can be provided as separate elements, or as a single piece of elastic material. Alternately, a single elastic element can be employed, or more than two elastic elements acting in concert.

In this embodiment, the elastic members 30 are positioned generally in the seat portion of the diaper. In practice, approximately the rear two-thirds of the diaper absorbent panel (i.e., the central and rear portions of the panel) are positioned generally beneath the seat of the wearer during use. Therefore, the provision of the centering gather arrangement in this region is preferred.

As will be appreciated, the one or more elastic elements which provide the center gathering force for the present diaper construction may be provided in many different forms. The term "elastic", as used herein, refers to sheets, films, ribbons, elastic hot-melt adhesives, elastomeric foam and nettings and the like which have a recovery of at least 50 percent, when elongated at least 10 percent of their yield point and measured in accordance with the following formula:

$$\text{Percent retraction} = \frac{(L_e - L_t)}{(L_e - L_o)} \times 100$$

where $L_o$ = original length of sample
$L_e$ = fully extended length
$L_t$ = length of sample measured three seconds after released from extended length.

The thickness of monofilament elastic members is generally 10 mils or less. The thickness of elastic film material is typically about 0.5 to 2.0 mils. Elastomeric foam materials typically have a thickness of 1-2 mm. The elastic members have an extensibility to rupture of at least about 150 percent, and a recovery at 50 percent elongation of at least about 50 percent, and preferably at least about 75 percent.

Elastic film elements suitable as gathering means for the diapers contemplated herein can be extruded to the desired thickness utilizing unvulcanized, thermoplastic compositions which are made up of an elastomeric component and an optional compatible modifier which is a thermoplastic polymer of a relatively low molecular weight but solid at ambient temperature.

Elastic film elements are highly thermoplastic and, though elastomeric, are unlike rubber in that the film can exhibit a relatively sharp melting point and is capable of being heat shaped. Also, the elastic elements can form permanent heat seals to substrates such as non-woven fabrics, or the like, at relatively low heat sealing peak temperatures, generally not above about 350° F. The elements are highly elastic and have a relatively low rubber modulus, i.e., they exhibit in at least one direction an elastic recovery from 50 percent stretch to at least 75 percent, preferably at least about 80 percent, and a 50 percent rubber modulus of not above about 2000 pounds per square inch, preferably not above 1000 pounds per square inch at 50 percent elongation. The film elements also are very flexible, extensible and soft and normally exhibits a Gurley stiffness of about one or less at a film thickness of one mil, and an elongation to break of at least about 150 percent, preferably at least about 400 percent, in at least one direction at ambient temperatures.

The manner in which the elastic members 30 or their equivalent gathering means are secured within the diaper structure can be widely varied while keeping with the teachings herein. In some applications, it can be desirable to secure the elastic elements to the associated layers of the diaper substantially along the entire length of the elastic elements, continuously, intermittently, and by distinct patterns of securement. Alternately, the elastic members may be secured only at their ends to the associated layers of the diaper. Various securement techniques can be employed, such as adhesive bonding, heat bonding, or ultrasonic bonding. While the elastic members can be positioned to exert the desired gathering force on various components of the diaper, operatively associating the elastic with at least the backing layer 16, or the barrier layer 28 is presently preferred.

In the embodiment illustrated in FIGS. 1-3, an arrangement is provided whereby the elastic members 30 are positioned between the backing layer 16 and the barrier layer 28. The elastic members are configured to create the desired longitudinal gathering force such as by securement to the backing layer 16 and/or the barrier layer 28, either at the ends of the elastic members or along the lengths thereof. A glue line 32 (FIG. 3) which extends longitudinally of the diaper between and separating the elastic elements 30, and which secures the backing layer 16 to the barrier layer 28 can optionally be provided.

Alternate securement arrangements for the one or more elastic members 30 can be employed. For example, suitable glue lines can be provided adjacent each member to form one or more tunnel-like channels within which the elastic members extend, thereby maintaining the members in the desired position while lending stability to the structure. If desired, the elastic members can be provided in the form of an elongated loop trained about a glue line such as 32, with such a loop imparting the desired gathering force to the associated components.

Referring to FIG. 4, an alternate diaper structure 110 is disclosed which illustrates an alternate construction in the region of the center gathers. In this diaper 110, components thereof which are the same as in the previously described embodiment are so-designated by like reference numerals. However, in this embodiment a pair of elastic members 130 are provided between the barrier layer 28 and the backing layer 16 with a line of securement 132 provided which may comprise adhesive bonding, ultrasonic bonding or the like, and which acts to secure the elastic members in position for contraction of the associated diaper structure. Securement 132 can extend longitudinally of the diaper, or may comprise spaced-apart regions of securement between facing layer 12, absorbent panel 14, barrier layer 28, and backing layer 16.

FIG. 5 illustrates a further alternate embodiment of the present-disposable diaper, designated 210, with like reference numerals employed to designate those components which are the same as in the previously described embodiments. In the embodiment of FIG. 5, a pair of longitudinally extending elastic members 230 are provided, which in this embodiment are positioned between absorbent panel 14 and barrier layer 28. As in the embodiment of FIG. 4, securement 232 extends between the facing layer 12, absorbent panel 14, barrier layer 28, and the backing layer 16 to integrate and unify the structure.

Referring to FIG. 2a, therein is illustrated a disposable diaper embodying the principles of the present invention. As will be recognized by those familiar with the art, this illustration (which closely corresponds to a photograph of a diaper embodying the present invention fitted to a baby) clearly shows the improved fit and body conformity provided by a diaper embodying the principles or the present invention. Rather than the usual bagginess or sagging at the medial portion of the diaper, it will be observed that the centrally disposed gathers in accordance with the present invention provide a very distinct line of gathering generally at G along the longitudinal centerline of the diaper construction. As discussed, this line of gathering G has been found to provide improved mobility for the wearer, and also facilitates convenient and comfortable fitting of clothing over the diaper article. The improved fit achieved with the present center gather arrangement can be particularly useful in eliminating the typical creases formed in a diaper's absorbent panel attendant to the usual folding and packaging of the product.

Figure 7:
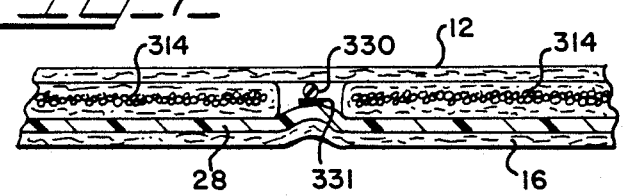
FIG. 7 is a fragmentary, cross-sectional view taken generally along lines 7—7 of FIG. 6.
Figure 8:
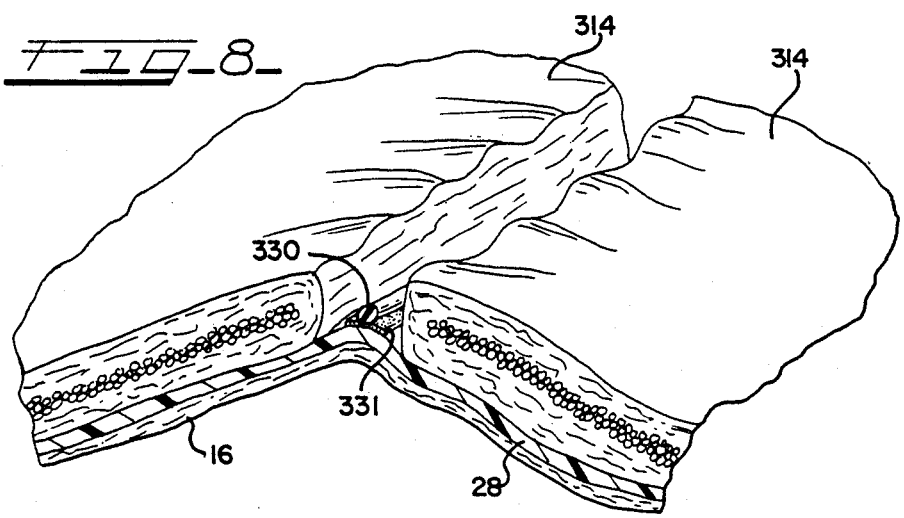
FIG. 8 is a diagrammatic view further illustrating the embodiment of FIG. 6.

Referring now to FIGS. 6-8, therein is illustrated a further alternate embodiment of the present disposable diaper, designated 310. Again, elements of this embodiment which are substantially the same as in the previous embodiments are so-designated by like reference numerals. As will be described, this embodiment includes an absorbent panel comprising a plurality of laterally adjacent, discrete panel sections, which panel sections cooperate with the center gathering means of the present invention to further enhance the fit and comfort of a disposable diaper embodying the principles of the present invention.

Referring first to FIG. 6, showing a top plan view, partially cutaway, of the disposable diaper 310, it will be observed that the absorbent panel structure of the diaper 310 is provided in the form of a pair of laterally adjacent, discrete panel sections 314 which are positioned between the facing layer 12 and the barrier layer 28. This embodiment further includes an elastic member 330 to provide the desired longitudinal gathering force on the absorbent panel structure, with the elastic member 330 extending generally along the longitudinal centerline of the panel, and generally at the adjacent inner edges of the panel sections 314. In accordance with the previous embodiments, the elastic member 330 preferably is positioned rearwardly of the front portion (i.e., front one-third) of the absorbent panel structure, and extends generally along the central and rear portions of the panel structure As will be appreciated, the provision of the absorbent panel in this sectionalized form permits the absorbent panel to further conform to the wearer of the diaper under the influence of the longitudinal gathering force created by the elastic member 330. This is diagrammatically illustrated in FIG. 8, wherein the puckering, or gathering of the inner adjacent edges of the panel sections 114 under the influence of elastic member 330 is illustrated. In this illustrated embodiment, the elastic member 330 is secured to the barrier layer 28 by adhesive 331 or like securement means, with the elastic member 330 further being optionally secured to the facing layer 12. Securement of the elastic member 330 to the facing layer is preferred for its aesthetic appearance, since it acts to desirably maintain the facing layer in intimate association with the absorbent panel structure. However, such securement is not necessary to achieve the desired improved fit and comfort provided by the present center gather arrangement.

As noted above, it is contemplated that the present absorbent article may include an absorbent panel structure provided in a wide variety of forms. As also noted, one form in which the absorbent panel may be provided is in accordance with the U.S. Pat. No. 4,573,988, to Pieniak, which discloses a compressed composite absorbent structure including a resilient web of fibers having incorporated therein superabsorbent material. Notably, this type of compressed composite absorbent structure particularly lends itself to use in the form of panel sections such as 114.

While it is contemplated that such discrete panel sections 114 can be provided as separate elements, which may be positioned either in contact with each other, or be spaced apart by a distance such as from one-eighth inch to one inch, it will further be appreciated that the discrete panel sections can alternately be provided by selectively weakening a unitary panel, such as by slitting or the like, along a line where elastic member 330 is provided. Further, conformity of the panel sections 114 to the wearer can be additionally enhanced such as by slitting or otherwise weakening the panel sections along their adjacent inner edges, such as illustrated by slits 115 shown in phantom line, thereby further enhancing the longitudinal gathering or "shirring" effect provided by the elastic member 30. Additionally, increased flexibility of the edge portions of the panel sections can be achieved in some types of absorbent structures by reducing the quantity of or eliminating the superabsorbent material at the edge portions.

As will be appreciated, the relative spacing of the panel sections can be appropriately varied depending upon the relative panel stiffness. If the panel sections are relatively stiff, a relatively wide spacing is preferred so that the backing and facing layers can be gathered to achieve the desired shaping of the article. Conversely, relatively flexible panel sections (or sections rendered flexible at the edges) permit a relatively closer spacing together of the sections.

Figure 9:
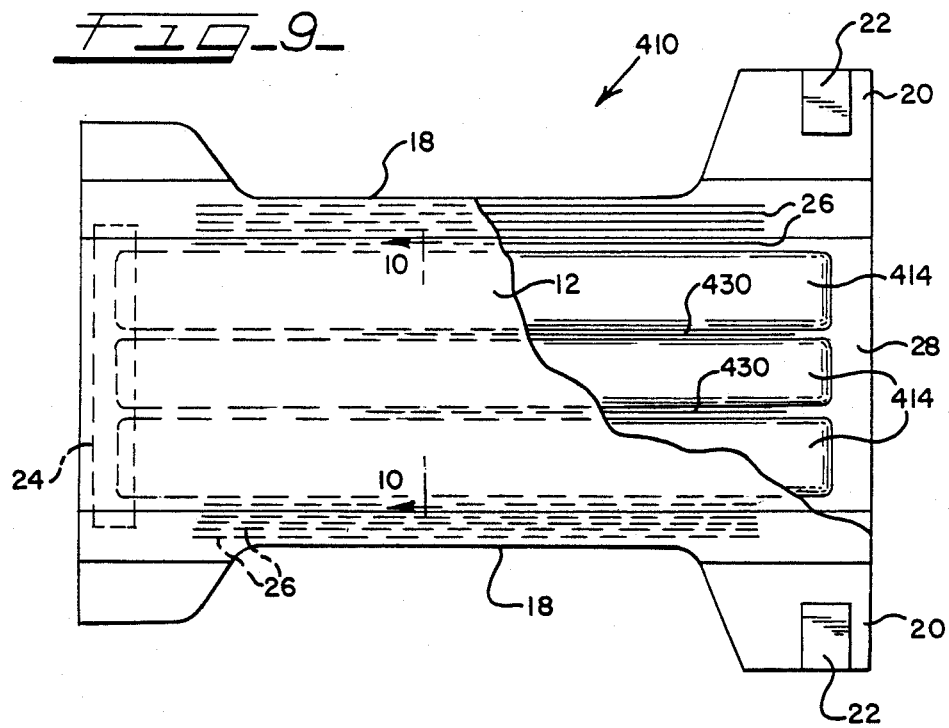
FIG. 9 is a top plan view of a further alternate construction of a disposable diaper embodying the present invention.
Figure 10:
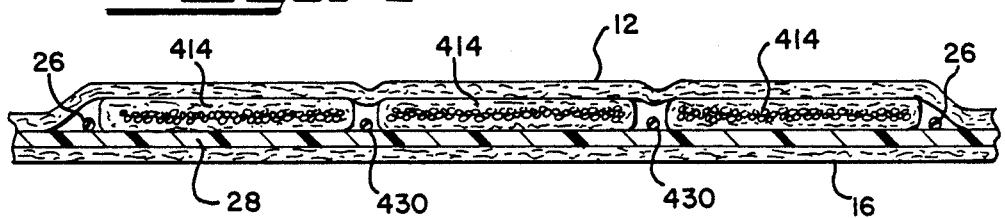
FIG. 10 is a cross-sectional view taken generally along lines 10-10 of FIG. 9.
Figure 11:
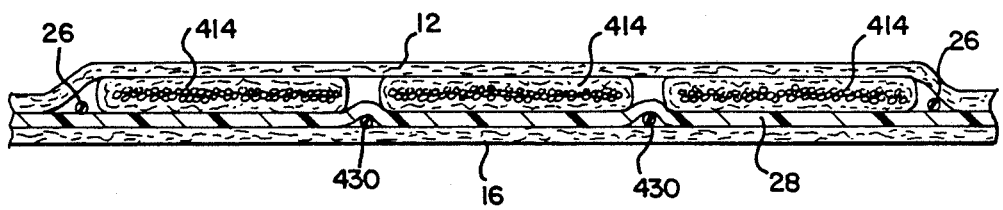
FIG. 11 is a cross-sectional view similar to FIG. 10 showing a modified form of the embodiment of FIG. 9.

Referring to FIGS. 9-11, therein is illustrated a further embodiment of a disposable diaper embodying the principles of the present invention, designated 410. Elements of this embodiment which are substantially the same as in the previous embodiments are so-designated by like reference numerals.

In the embodiment of FIG. 9, disposable diaper 410 is also provided with a sectionalized absorbent panel structure, in this embodiment comprising a plurality of laterally adjacent panel sections 414, including a center panel section and a pair of side panel sections positioned on respective opposite sides of the central panel section. In the illustrated form, each panel section 414 generally comprises one-third of the panel structure, divided width-wise.

In this embodiment, the center gather arrangement of the diaper comprises an elastic member 430 positioned generally at the adjacent edges of adjacent ones of the panel sections 414, i.e., at respective opposite lateral edges of the center panel section 414. As in previous embodiments, it is presently preferred that the elastic members 430 be positioned rearwardly of the front portion of the absorbent panel, and thus extend generally along the rear two-thirds of the panel structure, i.e., along the central and rear portions of the panel structure.

As in the previous embodiments, the center gather elastic members can be variously positioned in association with the panel structure for effecting the desired longitudinal gathering force. In the cross-sectional view of FIG. 10, it will be observed that the elastic members 430 are positioned above the barrier layer 28, generally between adjacent ones of the panel sections 414. In an alternate structure illustrated in FIG. 11, the elastic members 430 are positioned between the barrier layer 28 and the backing layer 16, again generally at adjacent edges of adjacent ones of the panel sections 414, i.e., on respective opposite sides of the center one of the panel sections 414.

As will be appreciated, this embodiment of the present diaper, including three side-by-side panel sections 414, can desirably be configured so as to shape the center panel section into a pocket or trough-like configuration, under the influence of elastic members 430. This can desirably enhance the liquid-holding impact capacity of the diaper. Further, the provision of this trough-like arrangement can be particularly advantageous with panel structures including superabsorbents. Since superabsorbents generally are most effective with high liquid concentrations, retention of liquid within the trough arrangement promotes free swelling of the superabsorbent material.

Referring now to FIG. 12, a further alternate embodiment of a disposable diaper embodying the principles of the present invention is shown, designated 510. Again, like reference numerals are used for those elements of the construction substantially the same as in the previous embodiments.

As in the embodiment of FIG. 9, the panel structure of the diaper 510 includes three laterally adjacent panel sections 514, with a center panel section positioned intermediate a pair of side panel sections. Further, an elastic member 530 is positioned generally between each adjacent pair of the panel sections 514, with the elastic members 530 thus positioned generally on respective opposite sides of the center panel section.

As will be observed, the elastic members 530 are positioned generally forwardly of the rear portion of the absorbent panel, and thus extend along the front and central portions of the panel structure. This arrangement desirably acts to shape the center panel section 514 to a trough-like configuration, as discussed above. As in the embodiment of FIG. 9, the embodiment of FIG. 12 is configured such that each of the panel sections 514 comprises approximately one-third of the overall panel structure.

Referring to the cross-sectional view of FIG. 13, it will be observed that the elastic members 530 are secured to the facing layer 12, by means of suitable adhesive or like bonding (not shown).

In order to further enhance the gathering effect provided by elastic members 530, diaper 510 further includes another elastic member 533 positioned beneath the center one of the panel sections 514, and extending generally along the longitudinal centerline of the diaper. As illustrated, elastic member 533 preferably is positioned to extend at least along the central and rear portions of the panel structure, and can be arranged to extend substantially the full length of the panel structure. By this arrangement, the desired longitudinal gathering of the diaper is provided generally along the seat portion thereof, with such gathering further provided by the elastic members 530 generally at the central and front portions of the absorbent panel structure. This effect is illustrated in FIG. 15, wherein lines of gathering G are formed. As will be observed, it is presently preferred that the end of the elastic member 533 be spaced from the back marginal edge of the diaper structure, to thereby minimize the effect of the elastic member on any waist gather which may be provided in the diaper structure. As will be appreciated, the tensional forces provided by the elastic members 530, and the member 533 can be different so as to shape the diaper in the desired manner.

Referring to FIG. 14, therein is a modified form of the embodiment of FIG. 13. As will be observed, this arrangement includes a center panel section 514' which is narrower than the laterally adjacent side panel sections 514. Again, this modification facilitates the desired gathering effect, enhancing the conformance provided by the present diaper structure.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure is intended to cover by the appended claims all such modifications as fall within the scope of the claims.

What is claimed is:

1. A disposable diaper having improved fit and comfort for the wearer, comprising:
an absorbent panel, said absorbent panel including a front portion, a rear portion, and a central portion extending therebetween, said absorbent panel comprising a pair of laterally adjacent, discrete panel sections;
a fluid-pervious facing layer positioned adjacent to and overlying one side of said absorbent panel, said facing layer being adapted for positioning in contact with the wearer of the diaper;
a backing layer positioned on the other side of said absorbent panel; leg-gathering means positioned generally at the laterally opposite margins of said disposable diaper to conform the diaper to the legs of the wearer; and
center gathering means operatively associated with said absorbent panel of said disposable diaper for providing a longitudinal gathering force on said absorbent panel so that the diaper conforms to the wearer for improved fit and comfort, said gathering means comprising elastic means positioned generally rearwardly of said front portion of said absorbent panel and extending generally longitudinally of said disposable diaper along said central and rear portions of said absorbent panel for providing said gathering force on said absorbent panel.

2. A disposable diaper in accordance with claim 1, including
a substantially fluid-impervious barrier layer interposed between said absorbent panel and said backing layer.

3. A disposable diaper in accordance with claim 2, wherein
said fluid-impervious barrier layer comprises a sheet of substantially fluid-impervious material interposed between said absorbent panel and said backing layer.

4. A disposable diaper in accordance with claim 1, wherein
said elastic means comprises at least one elastic member extending longitudinally of said disposable diaper along the longitudinal centerline thereof 5. A disposable diaper in accordance with claim 4, wherein
said elastic member is positioned beneath said absorbent panel and above said backing layer.

6. A disposable diaper in accordance with claim 1, wherein
said pair of laterally adjacent, discrete panel sections are provided as separate elements, said elastic member extending along the adjacent, inner edges of said discrete panel sections.

7. A disposable diaper in accordance with claim 1, wherein
said absorbent panel comprises a discrete, center panel section, and a pair of discrete side panel sections positioned on respective opposite lateral sides of said center panel section.

8. A disposable diaper in accordance with claim 7, wherein
said elastic means comprises at least one elastic member extending along the longitudinal centerline of said diaper beneath said center panel section, and said gathering means further comprises a pair of elastic members extending generally along respective opposite lateral edges of said center panel section.

9. An absorbent article having improved fit and comfort for the wearer, comprising:
an absorbent panel including a front panel, a rear portion, and a central portion extending therebetween, said absorbent panel comprising a plurality of laterally adjacent, discrete panel sections, including a discrete center panel section, and a pair of laterally adjacent, discrete side panel sections on respective opposite lateral sides of said center panel section;
a fluid-pervious facing layer positioned adjacent to and overlying one side of said absorbent panel, said facing layer being adapted for positioning adjacent to the wearer of the absorbent article;
a backing layer positioned on the other side of said absorbent panel; and
center gathering means for providing a longitudinal gathering force in said absorbent panel at least along said rear portion thereof so that the article conforms to the wearer for improved fit and comfort.

10. An absorbent article in accordance with claim 9, wherein
said gathering means comprising longitudinally extending elastic means positioned beneath said center panel section.

11. An absorbent article in accordance with claim 9, wherein
said center panel section is narrower than said side panel sections.

12. An absorbent article in accordance with claim 9, wherein
said center gathering means comprises an elastic member extending longitudinally along each adjacent pair of said discrete panel sections at the adjacent edges thereof.

13. An absorbent article in accordance with claim 12, wherein
said elastic members extend along the adjacent edges of each adjacent pair of said discrete panel sections and are positioned generally rearwardly of said front portion and extent along said central and rear portions.

14. An absorbent article in accordance with claim 12, wherein
said elastic members extend along the adjacent edges of each adjacent pair of said discrete panel sections and are positioned generally forwardly of said rear portion and extend along said central and front portions of said absorbent panel,
said center gathering means further comprising another elastic member extending longitudinally beneath said center panel section, and extending at least along said center and rear portions of said absorbent panel.

15. An absorbent article in accordance with claim 12, including
a substantially fluid-impervious barrier layer interposed between said absorbent panel and said backing layer.

16. An absorbent article in accordance with claim 12, wherein
said absorbent article comprises a disposable diaper and includes leg-gathering means positioned generally at the laterally opposite margins of said disposable diaper to conform the diaper to the legs of the wearer.

17. A disposable diaper in accordance with claim 1, including
means for increasing the flexibility of said adjacent panel sections along the adjacent edges thereof.

18. An absorbent article in accordance with claim 13, wherein
said center panel section and said side panel sections of said absorbent panel are provided as separate elements.

* * * * *